(12) United States Patent
Yokoyama et al.

(10) Patent No.: US 6,821,763 B2
(45) Date of Patent: Nov. 23, 2004

(54) PROCESS FOR PRODUCING MICROBIAL TRANSGLUTAMINASE

(75) Inventors: Keiichi Yokoyama, Kawasaki (JP);
Nami Nakamura, Kawasaki (JP);
Tetsuya Miwa, Kawasaki (JP);
Katsuya Seguro, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 423 days.

(21) Appl. No.: 09/884,948

(22) Filed: Jun. 21, 2001

(65) Prior Publication Data

US 2002/0173021 A1 Nov. 21, 2002

Related U.S. Application Data

(62) Division of application No. 09/448,310, filed on Nov. 24, 1999, now Pat. No. 6,538,122, which is a continuation of application No. 09/109,063, filed on Jul. 2, 1998, now Pat. No. 6,013,498.

(30) Foreign Application Priority Data

Jul. 4, 1997 (JP) .............................................. 9-180010

(51) Int. Cl.$^7$ ......................... C12N 9/10; A23C 19/032; A23C 9/137; A23L 1/06; A23L 1/054; A61K 7/00; A61K 38/45

(52) U.S. Cl. ....................... 435/193; 435/183; 424/401; 424/63; 424/69; 424/75; 424/78.03; 424/94.5; 426/36; 426/34; 426/42; 426/573; 426/582; 426/583; 426/656

(58) Field of Search ................................ 435/193, 183; 424/401, 69, 63, 75, 78.02, 94.5; 426/573, 577, 582, 583, 656

(56) References Cited

U.S. PATENT DOCUMENTS

| 5,156,956 | A |   | 10/1992 | Motoki et al. | ............. | 435/68.1 |
|---|---|---|---|---|---|---|
| 5,514,573 | A |   | 5/1996 | Yasueda et al. | ............. | 435/193 |
| 5,681,598 | A | * | 10/1997 | Kuraishi et al. | ............... | 426/36 |
| 5,731,183 | A |   | 3/1998 | Kobayashi et al. | ......... | 435/193 |
| 5,736,356 | A |   | 4/1998 | Sano et al. | ................ | 435/68.1 |
| 5,827,712 | A |   | 10/1998 | Yokoyama et al. | ......... | 435/193 |
| 6,013,498 | A |   | 1/2000 | Yokoyama et al. | ......... | 435/193 |

FOREIGN PATENT DOCUMENTS

| EP | 0 481 504 | 4/1992 |
|---|---|---|
| JP | 64-27471 | 1/1989 |
| JP | 1-50382 | 10/1989 |
| JP | 5-199883 | 8/1993 |
| JP | 6-30771 | 2/1994 |
| WO | WO 96/06931 | 3/1996 |
| WO | WO 96/22366 | 7/1998 |

OTHER PUBLICATIONS

A. Ben–Bassat, et al., Nature, vol. 326, p. 315, "Amino–Terminal Processing of Proteins", Mar. 19, 1987.

P. E. Devlin, et al., Gene, vol. 65, pp. 13–22, "Alteration of Amino–Terminal Condons of Human Granuloctye–Colony–Stimulating Factor Increases Expression Levels and Allows Efficient Processing by Methionine Aminopeptidase in *Escherichia coli*", 1988.

Shino Takeharo et al., "Chemical Synthesis of the Gene for Microbial Transglutaminase from *Streptoverticillium* and its Expression in *Escherichia coli*", Biosci. Biotech. Biochem., vol. 56, No. 1, pp. 88–92, 1994.

Misako Kawai et al., High–Level Expression of the Chemically Synthesized Gene for Microbial Transglutaminase from *Streptoverticillium* in *Escherichia coli*, Biosci. Biotech. Biochem., vol. 61, No. 5, pp. 830–835, May 1997.

Arie Ben–Bassat et al., "Processing of the Initiation Methionine from Proteins: Properties of the *Escherichia coli* Methionine Aminopeptidase and its Gene Structure", Journal of Bacteriology, vol. 169, No. 2, pp. 751–757, 1987.

Rochaide Othman et al., "Human Non–Pancreatic (Group II) Secreted Phospholipase $A_2$ Expressed from a Synthetic Gene in *Escherichia coli*: Characterisation of N–Terminal Mutants", Biochem. Biphys. Acta, vol. 1303, No. 2, pp. 92–102, 1996.

Koji Ikure et al., "Amino Acid Sequence of Guinea Pig Liver Transglutaminase Form its cDNA Sequence", Biochemistry, vol. 27, pp. 2898–2905, 1988.

M. A. Phillips et al., "Primary Structure of Keratinocyte Transglutaminase", Proc. Natl. Acad. Sci, USA, Vo. 87, pp. 9333–9337, Dec. 1990.

Atitada Ichinose et al., "Amino Acid Sequence of the A Subunit of Human Factor XII", Biochemistry, vol. 25, pp. 6900–6906, 1986.

* cited by examiner

*Primary Examiner*—Gabriele Bugaisky
(74) *Attorney, Agent, or Firm*—Oblon, Spivak, McClelland, Maier & Neustadt, P.C.

(57) ABSTRACT

Disclosed are a protein having a transglutaminase activity, which comprises a sequence ranging from serine residue at the second position to proline residue at the 331st position in an amino acid sequence represented by SEQ ID No. 1 wherein the N-terminal amino acid of the protein corresponds to serine residue at the second position of SEQ ID No. 1, a DNA encoding the protein, a transformant having the DNA, and a process for producing a protein having a transglutaminase activity, which comprises the steps of culturing the transformant in a medium. The protein can be produced in a large amount with the transformant using a host such as *E. coli*.

12 Claims, 7 Drawing Sheets

1. MTG (4 μg)

2. Whole fraction of broken pUC19/JM109 cells (negative control)

3. Whole fraction of broken pUCTRPMTG-02/JM109 cells

4. Centrifugal supernatant fraction of the third lane

5. Centrifugal precipitate fraction of the third lane

FIG. 7 pUCTRPMTG-02(+) : ...TTTAAATGGATTCTGACGAT...
                      M  D  S  D  D pUCTRPMTG(+)D2 : ...TTTAAATG----TCTGACGAT...
                      M        S  D  D

Natural MTG    :         D  S  D  D

---- are deleted bases

FIG. 8

MTG from pUCTRPMTG(+)D2 : SDDRV...

Reference
Natural MTG             : DSDDRV...
MTG from pUCTRPMTG-02(+) : MDSDDRV...

SEQUENCE LISTING

<160> NUMBER OF SEQ ID NOS: 62

<210> SEQ ID NO 1
<211> LENGTH: 331
<212> TYPE: PRT
<213> ORGANISM: Artificial Sequence
<220> FEATURE:
<223> OTHER INFORMATION: Description of Artificial
      Sequence:TRANSGLUTAMINASE

<400> SEQUENCE: 1

Asp Ser Asp Asp Arg Val Thr Pro Pro Ala Glu Pro Leu Asp Arg Met
 1               5                  10                  15

Pro Asp Pro Tyr Arg Pro Ser Tyr Gly Arg Ala Glu Thr Val Val Asn
                20                  25                  30

Asn Tyr Ile Arg Lys Trp Gln Gln Val Tyr Ser His Arg Asp Gly Arg
            35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
 65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 2
<211> LENGTH: 993
<212> TYPE: DNA
<213> ORGANISM: Artificial Sequence
<220> FEATURE:
<223> OTHER INFORMATION: Description of Artificial Sequence:SYNTHETIC DNA
<221> NAME/KEY: CDS
<222> LOCATION: (1)..(993)
<223> OTHER INFORMATION: IDENTIFICATION METHOD: S

<400> SEQUENCE: 2

| | | | | | | | | | | | | | | | | |
|---|---|---|---|---|---|---|---|---|---|---|---|---|---|---|---|---|
| gat | tct | gac | gat | cgt | gtt | act | cca | cca | gct | gaa | cca | ctg | gat | cgt | atg | 48 |
| Asp | Ser | Asp | Asp | Arg | Val | Thr | Pro | Pro | Ala | Glu | Pro | Leu | Asp | Arg | Met | |
| 1 | | | | 5 | | | | | 10 | | | | | 15 | | |
| cca | gat | cca | tat | cgt | cca | tct | tat | ggt | cgt | gct | gaa | act | gtt | gtt | aat | 96 |
| Pro | Asp | Pro | Tyr | Arg | Pro | Ser | Tyr | Gly | Arg | Ala | Glu | Thr | Val | Val | Asn | |
| | | | 20 | | | | | 25 | | | | | 30 | | | |
| aat | tat | att | cgt | aaa | tgg | caa | caa | gtt | tat | tct | cat | cgt | gat | ggt | cgt | 144 |
| Asn | Tyr | Ile | Arg | Lys | Trp | Gln | Gln | Val | Tyr | Ser | His | Arg | Asp | Gly | Arg | |
| | | 35 | | | | | 40 | | | | | 45 | | | | |
| aaa | caa | caa | atg | act | gaa | gaa | caa | cgt | gaa | tgg | ctg | tct | tat | ggt | tgc | 192 |
| Lys | Gln | Gln | Met | Thr | Glu | Glu | Gln | Arg | Glu | Trp | Leu | Ser | Tyr | Gly | Cys | |
| 50 | | | | | 55 | | | | | 60 | | | | | | |
| gtt | ggt | gtt | act | tgg | gtt | aac | tct | ggt | cag | tat | ccg | act | aac | cgt | ctg | 240 |
| Val | Gly | Val | Thr | Trp | Val | Asn | Ser | Gly | Gln | Tyr | Pro | Thr | Asn | Arg | Leu | |
| 65 | | | | 70 | | | | | 75 | | | | | 80 | | |
| gca | ttc | gct | tcc | ttc | gat | gaa | gat | cgt | ttc | aag | aac | gaa | ctg | aag | aac | 288 |
| Ala | Phe | Ala | Ser | Phe | Asp | Glu | Asp | Arg | Phe | Lys | Asn | Glu | Leu | Lys | Asn | |
| | | | 85 | | | | | 90 | | | | | 95 | | | |
| ggt | cgt | ccg | cgt | tct | ggt | gaa | act | cgt | gct | gaa | ttc | gaa | ggt | cgt | gtt | 336 |
| Gly | Arg | Pro | Arg | Ser | Gly | Glu | Thr | Arg | Ala | Glu | Phe | Glu | Gly | Arg | Val | |
| | | 100 | | | | | 105 | | | | | 110 | | | | |
| gct | aag | gaa | tcc | ttc | gat | gaa | gag | aaa | ggc | ttc | cag | cgt | gct | cgt | gaa | 384 |
| Ala | Lys | Glu | Ser | Phe | Asp | Glu | Glu | Lys | Gly | Phe | Gln | Arg | Ala | Arg | Glu | |
| | 115 | | | | | 120 | | | | | 125 | | | | | |
| gtt | gct | tct | gtt | atg | aac | cgt | gct | cta | gag | aac | gct | cat | gat | gaa | tct | 432 |
| Val | Ala | Ser | Val | Met | Asn | Arg | Ala | Leu | Glu | Asn | Ala | His | Asp | Glu | Ser | |
| 130 | | | | | 135 | | | | | 140 | | | | | | |
| gct | tac | ctg | gat | aac | ctg | aag | aag | gaa | ctg | gct | aac | ggt | aac | gat | gct | 480 |
| Ala | Tyr | Leu | Asp | Asn | Leu | Lys | Lys | Glu | Leu | Ala | Asn | Gly | Asn | Asp | Ala | |
| 145 | | | | 150 | | | | | 155 | | | | | 160 | | |
| ctg | cgt | aac | gaa | gat | gct | cgt | tct | ccg | ttc | tac | tct | gct | ctg | cgt | aac | 528 |
| Leu | Arg | Asn | Glu | Asp | Ala | Arg | Ser | Pro | Phe | Tyr | Ser | Ala | Leu | Arg | Asn | |
| | | | 165 | | | | | 170 | | | | | 175 | | | |
| act | ccg | tcc | ttc | aaa | gaa | cgt | aac | ggt | ggt | aac | cat | gat | ccg | tct | cgt | 576 |
| Thr | Pro | Ser | Phe | Lys | Glu | Arg | Asn | Gly | Gly | Asn | His | Asp | Pro | Ser | Arg | |
| | | 180 | | | | | 185 | | | | | 190 | | | | |
| atg | aaa | gct | gtt | atc | tac | tct | aaa | cat | ttc | tgg | tct | ggt | cag | gat | aga | 624 |
| Met | Lys | Ala | Val | Ile | Tyr | Ser | Lys | His | Phe | Trp | Ser | Gly | Gln | Asp | Arg | |
| | 195 | | | | | 200 | | | | | 205 | | | | | |
| tct | tct | tct | gct | gat | aaa | cgt | aaa | tac | ggt | gat | ccg | gat | gca | ttc | cgt | 672 |
| Ser | Ser | Ser | Ala | Asp | Lys | Arg | Lys | Tyr | Gly | Asp | Pro | Asp | Ala | Phe | Arg | |
| 210 | | | | 215 | | | | | 220 | | | | | | | |
| ccg | gct | ccg | ggt | act | ggt | ctg | gta | gac | atg | tct | cgt | gat | cgt | aac | atc | 720 |
| Pro | Ala | Pro | Gly | Thr | Gly | Leu | Val | Asp | Met | Ser | Arg | Asp | Arg | Asn | Ile | |
| 225 | | | | 230 | | | | | 235 | | | | | 240 | | |
| ccg | cgt | tct | ccg | act | tct | ccg | ggt | gaa | ggc | ttc | gtt | aac | ttc | gat | tac | 768 |
| Pro | Arg | Ser | Pro | Thr | Ser | Pro | Gly | Glu | Gly | Phe | Val | Asn | Phe | Asp | Tyr | |
| | | | 245 | | | | | 250 | | | | | 255 | | | |
| ggt | tgg | ttc | ggt | gct | cag | act | gaa | gct | gat | gct | gat | aag | act | gta | tgg | 816 |
| Gly | Trp | Phe | Gly | Ala | Gln | Thr | Glu | Ala | Asp | Ala | Asp | Lys | Thr | Val | Trp | |

-continued

```
                      260                 265                 270
acc cat ggt aac cat tac cat gct ccg aac ggt tct ctg ggt gct atg        864
Thr His Gly Asn His Tyr His Ala Pro Asn Gly Ser Leu Gly Ala Met
        275                 280                 285 cat gta tac gaa tct aaa ttc cgt aac tgg tct gaa ggt tac tct gac        912
His Val Tyr Glu Ser Lys Phe Arg Asn Trp Ser Glu Gly Tyr Ser Asp
    290                 295                 300 ttc gat cgt ggt gct tac gtt atc acc ttc att ccg aaa tct tgg aac        960
Phe Asp Arg Gly Ala Tyr Val Ile Thr Phe Ile Pro Lys Ser Trp Asn
305                 310                 315                 320 act gct ccg gac aaa gtt aaa cag ggt tgg ccg                            993
Thr Ala Pro Asp Lys Val Lys Gln Gly Trp Pro
                325                 330
```

<210> SEQ ID NO 3
<211> LENGTH: 1519
<212> TYPE: DNA
<213> ORGANISM: Artificial Sequence
<220> FEATURE:
<223> OTHER INFORMATION: Description of Artificial Sequence:SYNTHETIC DNA
<221> NAME/KEY: CDS
<222> LOCATION: (87)..(1082)

<400> SEQUENCE: 3

```
ttccctgtt gacaattaat catcgaacta gttaactagt acgcaagttc acgtaaaaag      60
ggtatcgatt agtaaggagg tttaaa atg gat tct gac gat cgt gtt act cca     113
                              Met Asp Ser Asp Asp Arg Val Thr Pro
                                1               5 cca gct gaa cca ctg gat cgt atg cca gat cca tat cgt cca tct tat      161
Pro Ala Glu Pro Leu Asp Arg Met Pro Asp Pro Tyr Arg Pro Ser Tyr
 10                  15                  20                  25 ggt cgt gct gaa act gtt gtt aat aat tat att cgt aaa tgg caa caa      209
Gly Arg Ala Glu Thr Val Val Asn Asn Tyr Ile Arg Lys Trp Gln Gln
                 30                  35                  40 gtt tat tct cat cgt gat ggt cgt aaa caa caa atg act gaa gaa caa      257
Val Tyr Ser His Arg Asp Gly Arg Lys Gln Gln Met Thr Glu Glu Gln
             45                  50                  55 cgt gaa tgg ctg tct tat ggt tgc gtt ggt gtt act tgg gtt aac tct      305
Arg Glu Trp Leu Ser Tyr Gly Cys Val Gly Val Thr Trp Val Asn Ser
         60                  65                  70 ggt cag tat ccg act aac cgt ctg gca ttc gct tcc ttc gat gaa gat      353
Gly Gln Tyr Pro Thr Asn Arg Leu Ala Phe Ala Ser Phe Asp Glu Asp
     75                  80                  85 cgt ttc aag aac gaa ctg aag aac ggt cgt ccg cgt tct ggt gaa act      401
Arg Phe Lys Asn Glu Leu Lys Asn Gly Arg Pro Arg Ser Gly Glu Thr
 90                  95                 100                 105 cgt gct gaa ttc gaa ggt cgt gtt gct aag gaa tcc ttc gat gaa gag      449
Arg Ala Glu Phe Glu Gly Arg Val Ala Lys Glu Ser Phe Asp Glu Glu
                110                 115                 120 aaa ggc ttc cag cgt gct cgt gaa gtt gct tct gtt atg aac cgt gct      497
Lys Gly Phe Gln Arg Ala Arg Glu Val Ala Ser Val Met Asn Arg Ala
            125                 130                 135 cta gag aac gct cat gat gaa tct gct tac ctg gat aac ctg aag aag      545
Leu Glu Asn Ala His Asp Glu Ser Ala Tyr Leu Asp Asn Leu Lys Lys
        140                 145                 150 gaa ctg gct aac ggt aac gat gct ctg cgt aac gaa gat gct cgt tct      593
Glu Leu Ala Asn Gly Asn Asp Ala Leu Arg Asn Glu Asp Ala Arg Ser
    155                 160                 165 ccg ttc tac tct gct ctg cgt aac act ccg tcc ttc aaa gaa cgt aac      641
Pro Phe Tyr Ser Ala Leu Arg Asn Thr Pro Ser Phe Lys Glu Arg Asn
```

```
                   170              175              180              185
ggt ggt aac cat gat ccg tct cgt atg aaa gct gtt atc tac tct aaa       689
Gly Gly Asn His Asp Pro Ser Arg Met Lys Ala Val Ile Tyr Ser Lys
                190              195              200 cat ttc tgg tct ggt cag gat aga tct tct tct gct gat aaa cgt aaa       737
His Phe Trp Ser Gly Gln Asp Arg Ser Ser Ser Ala Asp Lys Arg Lys
    205              210              215 tac ggt gat ccg gat gca ttc cgt ccg gct ccg ggt act ggt ctg gta       785
Tyr Gly Asp Pro Asp Ala Phe Arg Pro Ala Pro Gly Thr Gly Leu Val
        220              225              230 gac atg tct cgt gat cgt aac atc ccg cgt tct ccg act tct ccg ggt       833
Asp Met Ser Arg Asp Arg Asn Ile Pro Arg Ser Pro Thr Ser Pro Gly
            235              240              245 gaa ggc ttc gtt aac ttc gat tac ggt tgg ttc ggt gct cag act gaa       881
Glu Gly Phe Val Asn Phe Asp Tyr Gly Trp Phe Gly Ala Gln Thr Glu
250              255              260              265 gct gat gct gat aag act gta tgg acc cat ggt aac cat tac cat gct       929
Ala Asp Ala Asp Lys Thr Val Trp Thr His Gly Asn His Tyr His Ala
                270              275              280 ccg aac ggt tct ctg ggt gct atg cat gta tac gaa tct aaa ttc cgt       977
Pro Asn Gly Ser Leu Gly Ala Met His Val Tyr Glu Ser Lys Phe Arg
    285              290              295 aac tgg tct gaa ggt tac tct gac ttc gat cgt ggt gct tac gtt atc      1025
Asn Trp Ser Glu Gly Tyr Ser Asp Phe Asp Arg Gly Ala Tyr Val Ile
        300              305              310 acc ttc att ccg aaa tct tgg aac act gct ccg gac aaa gtt aaa cag      1073
Thr Phe Ile Pro Lys Ser Trp Asn Thr Ala Pro Asp Lys Val Lys Gln
            315              320              325 ggt tgg ccg taatgaaagc ttggatctct aattactgga cttcacacag              1122
Gly Trp Pro
330 actaaaatag acatatctta tattatgtga ttttgtgaca tttcctagat gtgaggtgga    1182 ggtgatgtat aaggtagatg atgatcctct acgccggacg catcgtggcc ggcatcaccg    1242 gcgccacagg tgcggttgct ggcgcctata tcgccgacat caccgatggg gaagatcggg    1302 ctcgccactt cgggctcatg agcgcttgtt tcggcgtggg tatggtggca ggccccgtgg    1362 ccggggggact gttgggcgcc atctccttgc atgcaccatt ccttgcggcg gcggtgctca   1422 acggcctcaa cctactactg gctgcttcc taatgcagga gtcgcataag ggagagcgtc     1482 gagagcccgc ctaatgagcg ggcttttttt tcagctg                            1519
```

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 4
aattcatcga ttagtaagga ggtttaaaat ggattctga                           39

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 5
cgatcgtcag aatccatttt aaacctcctt actaatcgat g            41

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 6
cgatcgtgtt actccaccag ctgaaccact ggatcgtatg c            41

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 7
gatctggcat acgatccagt ggttcagctg gtggagtaac a            41

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 8
cagatccata tcgtccatct tatggtcgtg ctgaaactgt t            41

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 9
attaacaaca gtttcagcac gaccataaga tggacgatat g            41

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 10
gttaataatt atattcgtaa atggcaacaa gtttattctc a            41

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 11

```
tcacgatgag aataaacttg ttgccattta cgaatataat t         41
```

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 12

```
tcgtgatggt cgtaaacaac aaatgactga agaacaacgt g         41
```

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 13

```
gccattcacg ttgttcttca gtcatttgtt gtttacgacc a         41
```

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 14

```
aatggctgtc ttatggttgc gttggtgtta cttgggttaa ca        42
```

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 15

```
agcttgttaa cccaagtaac accaacgcaa ccataagaca           40
```

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 16

```
aattcgttaa ctctggtcag tatccgacta accgtctg             38
```

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 17

```
cgaatgccag acggttagtc ggatactgac cagagttaac g         41
```

<210> SEQ ID NO 18
<211> LENGTH: 49
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 18
gcattcgctt ccttcgatga agatcgtttc aagaacgaac tgaagaacg            49

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 19
ggacgaccgt tcttcagttc gttcttgaaa cgatcttcat cgaaggaag            49

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 20
gtcgtccgcg ttctggtgaa actcgtgctg aattc                           35

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 21
gaccttcgaa ttcagcacga gtttcaccag aacgc                           35

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 22
gaaggtcgtg ttgctaagga atccttcgat gaagagaaag gcttccag             48

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 23
gagcacgctg gaagcctttc tcttcatcga aggattcctt agcaacac             48

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 24
cgtgctcgtg aagttgcttc tgttatgaac cgtgctctag aa                          42

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 25
agctttctag agcacggttc ataacagaag caacttcac                              39

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 26
aattctctag agaacgctca tgatgaatct gcttacctgg ataac                       45

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 27
cttcttcagg ttatccaggt aagcagattc atcatgagcg ttctctagag                  50

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 28
ctgaagaagg aactggctaa cggtaacgat gctctgcgta acgaagatg                   49

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 29
gagaacgagc atcttcgtta cgcagagcat cgttaccgtt agccagttc                   49

```
<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 30
ctcgttctcc gttctactct gctctgcgta acactccgtc                              40

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 31
ctttgaagga cggagtgtta cgcagagcag agtagaacg                               39

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 32
cttcaaagaa cgtaacggtg gtaaccatga tccgtctcgt atgaaag                      47

<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 33
gataacagct ttcatacgag acggatcatg gttaccaccg ttacgtt                      47

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 34
ctgttatcta ctctaaacat ttctggtctg gtcaggatag atcta                        45

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 35
agcttagatc tatcctgacc agaccagaaa tgtttagagt a                            41

<210> SEQ ID NO 36
```

```
<211> LENGTH: 42
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 36
aattcagatc ttcttctgct gataaacgta aatacggtga tc                    42

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 37
catccggatc accgtattta cgtttatcag cagaagaaga tctg                  44

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 38
cggatgcatt ccgtccggct ccgggtactg gtctggtaga catgtctc              48

<210> SEQ ID NO 39
<211> LENGTH: 48
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 39
gatcacgaga catgtctacc agaccagtac ccggagccgg acggaatg              48

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 40
gtgatcgtaa catcccgcgt tctccgactt ctccg                            35

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 41
cttcacccgg agaagtcgga gaacgcggga tgttac                           36

<210> SEQ ID NO 42
<211> LENGTH: 40
```

```
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 42
ggtgaaggct tcgttaactt cgattacggt tggttcggtg                          40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 43
gtctgagcac cgaaccaacc gtaatcgaag ttaacgaagc                          40

<210> SEQ ID NO 44
<211> LENGTH: 44
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 44
ctcagactga agctgatgct gataagactg tatggaccca tgga                     44

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 45
agcttccatg ggtccataca gtcttatcag catcagcttc a                        41

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 46
aattcccatg gtaaccatta ccatgctccg aacggttct                           39

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 47
cacccagaga accgttcgga gcatggtaat ggttaccatg gg                       42

<210> SEQ ID NO 48
<211> LENGTH: 41
<212> TYPE: DNA
```

<213> ORGANISM: Artificial Sequence
<220> FEATURE:
<223> OTHER INFORMATION: Description of Artificial Sequence:SYNTHETIC
      DNA

<400> SEQUENCE: 48
ctgggtgcta tgcatgtata cgaatctaaa ttccgtaact g                    41

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 49
cttcagacca gttacggaat ttagattcgt atacatgcat ag                   42

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 50
gtctgaaggt tactctgact tcgatcgtgg tgcttac                         37

<210> SEQ ID NO 51
<211> LENGTH: 37
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 51
gtgataacgt aagcaccacg atcgaagtca gagtaac                         37

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 52
gttatcacct tcattccgaa atcttggaac actgctcc                        38

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 53
ctttgtccgg agcagtgttc caagatttcg gaatgaag                        38

<210> SEQ ID NO 54
<211> LENGTH: 38
<212> TYPE: DNA
<213> ORGANISM: Artificial Sequence

```
<220> FEATURE:
<223> OTHER INFORMATION: Description of Artificial Sequence:SYNTHETIC
      DNA

<400> SEQUENCE: 54
ggacaaagtt aaacagggtt ggccgtaatg aaagctta                              38

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 55
agcttaagct ttcattacgg ccaaccctgt ttaa                                  34

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 56
ttttcccagt cacgacgttg                                                  20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 57
caggaaacag ctatgaccat g                                                21

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 58
taaggaggtt taaaatgtct gacgatcgtg ttactc                                36

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 59
tacgccaagg ttgttaaccc a                                                21

<210> SEQ ID NO 60
<211> LENGTH: 5
<212> TYPE: PRT
<213> ORGANISM: Artificial Sequence
<220> FEATURE:
```

-continued

```
<223> OTHER INFORMATION: Description of Artificial Sequence:N-TERMINAL
      FRAGMENT

<400> SEQUENCE: 60

Ser Asp Asp Arg Val
  1               5

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence:CODON FOR
      N-TERMINAL FRAGMENT

<400> SEQUENCE: 61
tctgacgatc gtgtt                                                    15

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence:N-TERMINAL
      FRAGMENT

<400> SEQUENCE: 62

Met Ser Asp Asp Arg
  1               5
```

PROCESS FOR PRODUCING MICROBIAL TRANSGLUTAMINASE

This application is a Divisional of Ser. No. 09/448,310 filed Nov. 24, 1999, now U.S. Pat. No. 6,538,122 which is a Continuation of Ser. No. 09/109,063 fIled Jul. 2, 1998, now U.S. Pat. No. 6,013,498.

BACKGROUND OF THE INVENTION

The present invention relates to a protein having a transglutaminase activity, DNA which encodes for the protein, and a process for producing the protein. In particularly, the present invention relates to a process for producing a protein having a transglutaminase activity by a genetic engineering technique.

Transglutaminase is an enzyme which catalyzes the acyl transfer reaction of a γ-carboxyamido group in a peptide chain of a protein. When such an enzyme react with the protein, a reaction of an ε-(γ-Glu)-Lys forming reaction or substitution reaction of Gln with Glu by the deamidation of Glu can occur.

The transglutaminase is used for the production of gelled foods such as jellies, yogurts, cheeses, gelled cosmetics, etc. and also for improving the quality of meats [see Japanese Patent Publication for Opposition Purpose (hereinafter referred to as "J. P. KOKOKU") No. Hei 1-50382]. The transglutaminase is also used for the production of a material for microcapsules having a high thermal stability and a carrier for an immobilized enzyme. The transglutaminase is thus industrially very useful.

As for transglutaminases, those derived from animals and those derived from microorganisms (microbial transglutaminase; hereinafter referred to as "MTG") have been known hitherto.

The transglutaminases derived from animals are calcium ion-dependent enzymes which are distributed in organs, skins and bloods of animals. They are, for example, guinea pig liver transglutaminase [K. Ikura et al., Biochemistry 27, 2898 (1988)], human epidermis keratin cell transglutaminase [M. A. Philips et al., Proc. Natl. Acad. Sci. USA 87, 9333 (1990)] and human blood coagulation factor XIII (A. Ichinose et al., Biochemistry 25, 6900 (1990)].

As for the transglutaminases derived from microorganisms, those independent on calcium were obtained from microorganisms of the genus *Streptoverticillium*. They are, for example, *Streptoverticillium griseocarneum* IFO 12776, *Streptoverticillium cinnamoneum* sub sp. *cinnamoneum* IFO 12852 and *Streptoverticillium mobaraense* IFO 13819 [see Japanese Patent Unexamined Published Application (hereinafter referred to as "J. P. KOKAI") No. Sho 64-27471].

According to the peptide mapping and the results of the analysis of the gene structure, it was found that the primary structure of the transglutaminase produced by the microorganism is not homology with that derived from the animals at all (European Patent publication No. 0 481 504 A1).

Since the transglutaminases (MTG) derived from microorganisms are produced by the culture of the above-described microorganisms followed by the purification, they had problems in the supply amount, efficiency, and the like. It is also tried to produce them by a genetic engineering technique. This technique includes a process which is conducted by the secretion expression of a microorganism such as *E. coli*, yeast or the like (J. P. KOKAI No. Hei 5-199883), and a process wherein MTG is expressed as an inactive fusion protein inclusion body in *E. coli*, this inclusion body is solubilized with a protein denaturant, the denaturant is removed and then MTG is reactivated to obtain the active MTG (J. P. KOKAI No. Hei 6-30771).

However, these processes have problems when they are practiced on an industrial scale. Namely, when the secretion by the microorganisms such as *E. coli* and yeast is employed, the amount of the product is very small; and when MTG is obtained in the form of the inactive fusion protein inclusion body in *E. coli*, an expensive enzyme is necessitated for the cleavage.

It is known that when a foreign protein is secreted by the genetic engineering method, the amount thereof thus obtained is usually small. On the contrary, it is also known that when the foreign protein is produced in the cell of *E. coli*, the product is in the form of inert protein inclusion body in many cases although the expressed amount is high. The protein inclusion body must be solubilized with a denaturant, the denaturating agent must be removed and then MTG must be reactivated.

It is already known that in the expression in *E. coli*, an N-terminal methionine residue in natural protein obtained after the translation of gene is efficiently cleaved with methionine aminopeptidase. However, the N-terminal methionine residue is not always cleaved in an exogenous protein.

Processes proposed hitherto for obtaining a protein free from N-terminal methionine residue include a chemical process wherein a protein having methionine residue at the N-terminal or a fusion protein having a peptide added thereto through methionine residue is produced and then the product is specifically decomposed at the position of methionine residue with cyanogen bromide; and an enzymatic process wherein a recognition sequence of a certain site-specific proteolytic enzyme is inserted between a suitable peptide and an intended peptide to obtain a fusion peptide, and the site-specific hydrolysis is conducted with the enzyme.

However, the former process cannot be employed when the protein sequence contains a methionine residue, and the intended protein might be denatured in the course of the reaction. The latter process cannot be employed when a sequence which is easily broken down is contained in the protein sequence because the yield of the intended protein is reduced. In addition, the use of such a proteolytic enzyme is unsuitable for the production of protein on an industrial scale from the viewpoint of the cost.

Conventional processes for producing MTG have many problems such as supply amount and cost. Namely, in the secretion expression by *E. coli*, yeast or the like, the expressed amount is disadvantageously very small. In the production of the fusion protein inclusion body in *E. coli*, it is necessary, for obtaining mature MTG, to cleave the fusion part with restriction protease after the expression. Further, it has been found that since MTG is independent on calcium, the expression of active MTG in the cell of a microorganism is fatal because this enzyme acts on the endoprotein.

Thus, for the utilization of MTG, produced by the gene recombination, on an industrial scale, it is demanded to increase the production of mature MTG free of the fusion part. The present invention has been completed for this purpose. The object of the present invention is to product MTG in a large amount in microorganisms such as *E. coli*.

When MTG is expressed with recombinant DNA of the present invention, methionine residue is added to the N-terminal of MTG. However, by the addition of the methionine residue to the N-terminal of MTG, there is some possibility wherein problems of the safety such as impartation of antigenicity to MTG occur. It is another problem to be solved by the present invention to produce MTG free of methionine residue corresponding to the initiation codon.

SUMMARY OF THE INVENTION

An object of the present invention is to provide a novel protein having a transglutaminase activity.

Another object of the present invention is to provide a DNA encoding for the novel protein having a transglutaminase activity.

Another object of the present invention is to provide a recombinant DNA encoding for the novel protein having a transglutaminase activity.

Another object of the present invention is to provide a transformant obtained by the transformation with the recombinant DNA.

Another object of the present invention is to provide a process for producing a protein having a transglutaminase activity.

These and other objects of the present invention will be apparent from the following description and examples.

For solving the above-described problems, the inventors have constructed a massive expression system of protein having transglutaminase activity by changing the codon to that for *E. coli*, or preferably by using a multi-copy vector (pUC19) and a strong promoter (trp promoter).

Since MTG is expressed and secreted in the prepro-form from microorganisms of actinomycetes, the MTG does not have methionine residue corresponding to the initiation codon at the N-terminal, but the protein expressed by the above-described expression method has the methionine residue at the N-terminal thereof. To solve this problem, the inventors have paid attention to the substrate specificity of methionine aminopeptidase of *E. coli*, and succeeded in obtaining a protein having transglutaminase activity and free from methionine at the N-terminal by expressing the protein in the form free from the aspartic acid residue which is the N-terminal amino acid of MTG. The present invention has been thus completed.

Namely, the present invention provides a protein having a transglutaminase activity, which comprises a sequence ranging from serine residue at the second position to proline residue at the 331st position in an amino acid sequence represented by SEQ ID No. 1 wherein N-terminal amino acid of the protein corresponds to serine residue at the second position of SEQ ID No. 1.

There is provided a protein which consists of an amino acid sequence of from serine residue at the second position to proline residue at the 331st position in an amino acid sequence of SEQ ID No. 1.

There is provided a DNA which codes for said proteins.

There is provided a recombinant DNA having said DNA, in particular, a recombinant DNA expressing said DNA.

There is provided a transformant obtained by the transformation with the recombinant DNA.

There is provided a process for producing a protein having a transglutaminase activity, which comprises the steps of culturing the transformant in a medium to produce the protein having a transglutaminase activity and recovering the protein.

Taking the substrate specificity of methionine aminopeptidase into consideration, the process for producing the protein having transglutaminase activity and free of initial methionine is not limited to the removal of the N-terminal aspartic acid.

BRIEF EXPLANATION OF THE DRAWINGS

FIG. 7 shows that GAT corresponding to Aspartic acid residue is deleted.

FIG. 8 shows that N-terminal amino acid is serine.

DETAILED DESCRIPTION OF THE PREFERRED EMBODIMENTS

Figure 1:
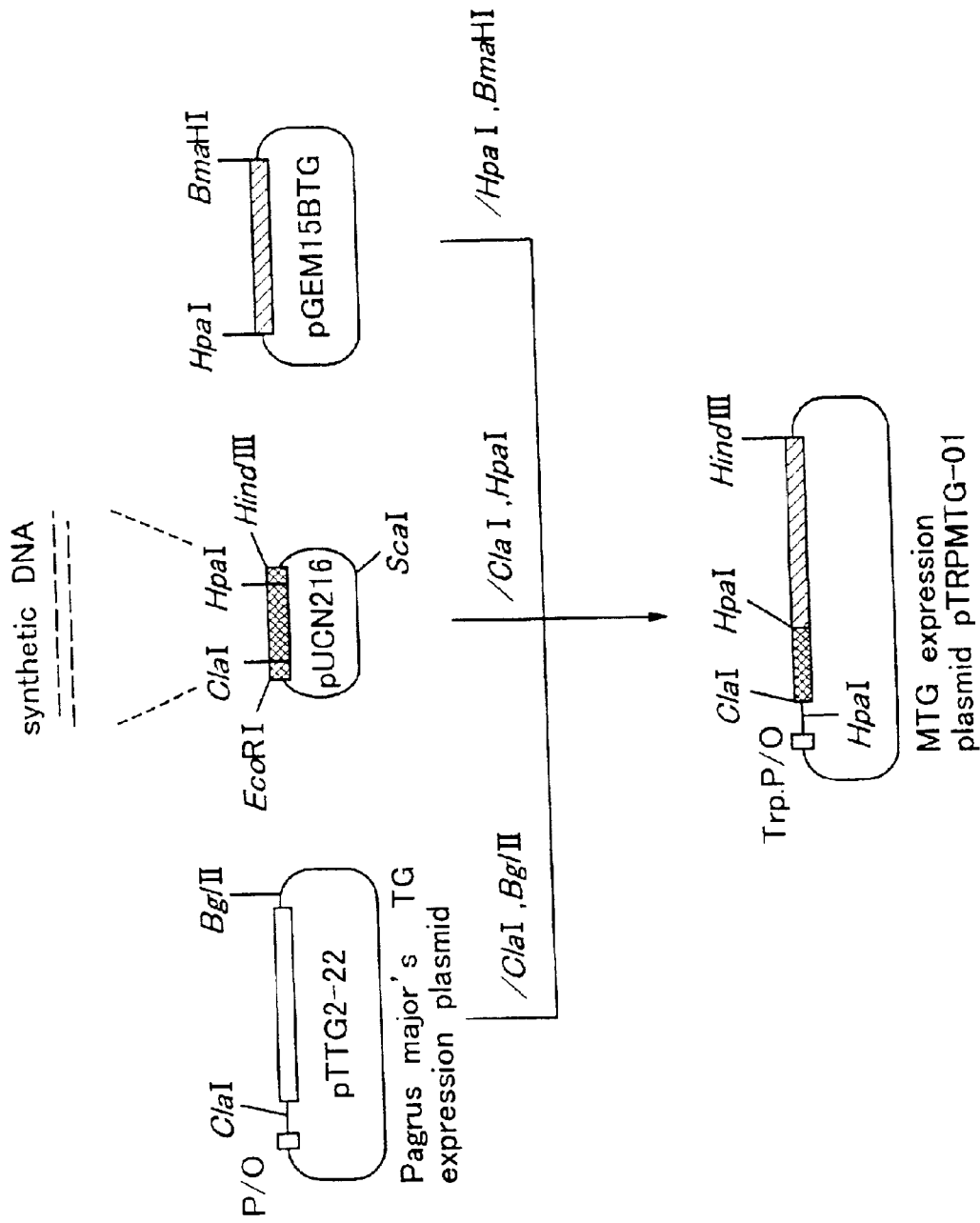
FIG. 1 shows a construction scheme of MTG expression plasmid pTRPMTG-01.

The proteins having a transglutaminase activity according to the present invention comprise a sequence ranging from serine residue at the second position to proline residue at the 331st position in an amino acid sequence represented by SEQ ID No. 1 as an essential sequence but the protein may further have an amino acid or amino acids after proline residue at the 331st position. Among these, the preferred is a protein consisting of an amino acid sequence of from serine residue at the second position to proline residue at the 331st position in an amino acid sequence of SEQ ID No. 1.

In these amino acid sequences, the present invention includes amino acid sequences wherein an amino acid or some amino acids are deleted, substituted or inserted as far as such amino acid sequences have a transglutaminase activity.

The DNA of the present invention encodes the above-mentioned proteins. Among these, the preferred is a DNA wherein a base sequence encoding for Arg at the forth position from the N-terminal amino acid is COT or CGC, and a base sequence encoding for Val at the fifth position from the N-terminal amino acid is GIT or GTA. Furthermore, the preferred is a DNA wherein a base sequence encoding for the N-terminal amino acid to fifth amino acid, Ser-Asp-Asp-Arg-Val, (SEQ ID NO: 62) has the following sequence.

```
Ser : TCT or TCC
Asp : GAC or GAT
Asp : GAC or GAT
Arg : CGT or CGC
Val : GTT or GTA
```

In this case, the preferred is a DNA wherein a base sequence encoding for amino acid sequence of from the N-terminal amino acid to fifth amino acid, Ser-Asp-Asp-Arg-Val, (SEQ ID NO: 60) has the sequence TCT-GAC-GAT-CGT-GTFI (SEQ ID NO: 61).

Furthermore, the preferred is a DNA wherein a base sequence encoding for amino acid sequence of from sixth amino acid to ninth amino acid from the N-terminal amino acid, Thr-Pro-Pro-Ala, has the following sequence.

```
Thr : ACT or ACC
Pro : CCA or CCG
Pro : CCA or CCG
Ala : GCT or GCA
```

Furthermore, the preferred is a DNA comprising a sequence ranging from thymine base at the fourth position to guanine base at the 993rd position in the base sequence of SEQ ID No. 2. In this case, more preferred is a DNA consisting of a sequence ranging from thymine base at the fourth position to guanine base at the 993rd position in the base sequence of SEQ ID No. 2.

In the DNA sequences mentioned above, nucleic acids encoding an amino acid or some amino acids may be deleted, substituted or inserted as far as such DNA encodes an amino acid sequence having a transglutaminase activity.

The recombinant DNA of the present invention has one of DNA mentioned above. In this case, the preferred is a DNA having a promoter selected from the group consisting of trp, tac, lac, trc, λ PL and T7.

The transformants of the present invention are obtained by the transformation with the above-mentioned recombinant DNA. Among these, it is preferable that a transformation be conducted by use of a multi-copy vector, and that the transformants belong to *Escherichia coli*.

The process for producing a protein having a transglutaminase activity according to the present invention comprises the steps of culturing one of the above-mentioned transformants in a medium to produce the protein having a transglutaminase activity and recovering the protein.

The detailed description will be further made on the present invention.

(1) It is known that the expression of MTG in the cells of a microorganism is fatal. It is also known that in the high expression of the protein in a microorganism such as *E. coli*, the expressed protein is inclined to be in the form of inert insoluble protein inclusion bodies. Under these circumstances, the inventors made investigations for the purpose of obtaining a high expression of MTG as an inert, insoluble protein in *E. coli*.

A structural gene of MTG used for achieving the high expression is a DNA containing a sequence ranging from thymine base at the fourth position to guanine base at the 993rd position in the base sequence of SEQ ID No. 2. Taking the degeneration of the genetic codon, the third letter in the degenerate codon in a domain which codes for the N-terminal portion is converted to a codon rich in adenine and uracil and the remaining portion is comprised of a codon frequently used for *E. coli* in order to inhibit the formation of high-order structure of mRNA, though a DNA which codes for proteins having the same amino acid sequence can have various base sequences.

A strong promoter usually used for the production of foreign proteins is used for the expression of MTG structural gene, and a terminator is inserted into the downstream of MTG structural gene. For example, the promoters are trp, tac, lac, trc, λ PL and T7, and the terminators are trpA, lpp and T4.

For the efficient translation, the variety and number in the SD sequence, and the base composition, sequence and length in the domain between the SD sequence and initiation codon were optimized for the expression of MTG.

The domain ranging from the promoter to the terminator necessitated for the expression of MTG can be produced by a well-known chemical synthesis method. An example of the base sequence is shown in SEQ ID No. 3. In the amino acid sequence of sequence No. 3, aspartic acid residue follows the initiation codon. However, this aspartic acid residue is preferably removed as will be described below.

The present invention also provides a recombinant DNA usable for the expression of MTG.

The recombinant DNA can be produced by inserting a DNA containing the structural gene of the above-described MTG in a known expression vector selected depending on a desired expression system. The expression vector used herein is preferably a multi-copy vector.

Known expression vectors usable for the production of the recombinant DNA of the present invention include pUC19 and pHSG299. An example of the recombinant DNA of the present invention obtained by integrating DNA of the present invention into pUC19 is pUCTRPMTG-02(+).

The present invention also relates to various transformants obtained by the introduction of the recombinant DNA.

The cells capable of forming the transformant include *E. coli* and the like.

An example of *E. coli* is the strain JM109 (recAl, endAl, gyrA96, thi, hsdR17, supE44, relAl,Δ(lac-proAB)/F' [traD36, proAB+, lacIq, lacZ ΔM15]).

A protein having a transglutaminase activity is produced by culturing the transformant such as that obtained by transforming *E. coli* JM109 with pUCTRPMTG-02(+) which is a vector of the present invention.

Examples of the medium used for the production include 2xYT medium used in the Example given below and medium usually used for culturing *E. coli* such as LB medium and M9-Casamino acid medium.

The culture conditions and production-inducing conditions are suitably selected depending on the kinds of the vector, promoter, host and the like. For example, for the production of a recombinant product with trp promoter, a chemical such as 3-β-indoleacrylic acid may be used for efficiently working the promoter. If necessary, glucose, Casamino acid or the like can be added in the course of the culture. Further, a chemical (ampicillin) resistant to genes which are resistant to chemicals kept in plasmid can also be added in order to selectively proliferate a recombinant *E. coli*.

The protein having a transglutaminase activity, which is produced by the above-described process, is extracted from the cultured strain as follows: After the completion of the culture, the cells are collected and suspended in a buffer solution. After the treatment with lysozyme, freezing/melting, ultrasonic disintegration, etc., the thus-obtained suspension of the disintegrated cells is centrifuged to divide it into a supernatant liquid and precipitates.

The protein having a transglutaminase activity is obtained in the form of a protein inclusion body and contained in the precipitates. This protein is solubilized with a denaturant or the like, the denaturant is removed and the protein is separated and purified. Examples of the denaturants usable for solubilizing the protein inclusion body produced as described above include urea (such as 8M) and guanidine hydrochloride (such as 6 M). After removing the denaturant by the dialysis or the like, the protein having a transglutaminase activity is regenerated. Solutions used for the dialysis are a phosphoric acid buffer solution, tris hydrochloride buffer solution, etc. The denaturant can be removed not only by the dialysis but also dilution, ultrafiltration or the like. The regeneration of the activity is expectable by any of these techniques.

After the regeneration of the activity, the active protein can be separated and purified by a suitable combination of well-known separation and precipitation methods such as salting out, dialysis, ultrafiltration, gel filtration, SDS-polyacrylamide electrophoresis, ion exchange chromatography, affinity chromatography, reversed-phase high-performance liquid chromatography and isoelectric point electrophoresis.

(2) The present invention provides a protein having a transglutaminase activity, which has a sequence ranging from serine residue at the second position to proline residue at the 331st position in the amino acid sequence represented in SEQ ID No. 1.

The N-terminals of MTG produced by the product transformed with recombinant DNA having a DNA represented in SEQ ID No. 3 was analyzed to find that most of them contained (formyl)methionine residue of the initiation codon.

However, when a gene which encodes for an exogenous protein is expressed in E. coli, the gene is designed so that the intended protein is positioned after the methionine residue encoded by ATG which is the translation initiation signal for the gene. It is already known that N-terminal methionine residues of a natural protein obtained by the translation from genes are more efficiently cut by methionine aminopeptidase. However, the N-terminal methionine residues are not always cut in the exogenous protein.

It is known that the substrate specificity of methionine aminopeptidase varies depending on the variety of the amino acid residue positioned next to the methionine residue. When the amino acid residue positioned next to the methionine residue is alanine residue, glycine residue, serine residue or the like, the methionine residue is easily cleaved, and when the former is aspartic acid, asparagine, lysine, arginine, leucine or the like, the latter is difficultly cleaved [Nature 326, 315(1987)].

The N-terminal amino acid residue of MTG is aspartic acid residue. When a methionine residue derived from the initiation codon is positioned directly before the aspartic acid residue, methionine aminopeptidase difficultly acts on the obtained sequence, and the N-terminal methionine residue is usually not removed but remains. However, since serine residue is arranged next to N-terminal aspartic acid in MTG, the sequence can be so designed that the amino acid residue positioned next to methionine residue derived from the initiation codon will be serine residue (an amino acid residue on which methionine aminopeptidase easily acts) by deleting aspartic acid residue. Thus, a protein having a high transglutaminase activity, from which the N-terminal methionine residue has been cleaved, can be efficiently produced.

The recombinant protein thus obtained is shorter than natural MTG by one amino acid residue, but the function of this protein is the same as that of the natural MTG. Namely, MTG activity is not lost by the lack of one amino acid. Although there is a possibility that a protein having a transglutaminase activity, from which the methionine residue has not been cleaved, gains a new antigenicity, it is generally understood that the sequence shortened by several residues does not gain a new antigenicity which natural MTG does not have. Thus, there is no problem of the safety.

In fact, a sequence of Met-Ser-Asp-Asp-Arg-... (SEQ ID NO: 62) was designed by deleting N-terminal aspartic acid residue from transglutaminase derived from microorganism (MTG), and this was produced in E. coli. As a result, methionine residue was efficiently removed and thereby there was obtained a protein having a sequence of Ser-Asp-Asp-Arg-... It was confirmed that the specific activity of the thus-obtained protein is not different from that of natural MTG.

A process for producing a protein having a transglutaminase activity, which has a sequence ranging from serine residue at the second position to proline residue at the 331st position in the amino acid sequence represented in SEQ ID No. 1 will be described below.

That is, a DNA which encodes for a protein having a transglutaminase activity and having a sequence ranging from serine residue at the second position to proline residue at the 331st position in the amino acid sequence represented in SEQ ID No. 1 is employed as the MTG structural gene present on recombinant DNA usable for the expression of MTG. Concretely, a DNA having a sequence ranging from thymine base at the fourth position to guanine base at the 993rd position in the base sequence of SEQ ID No. 2 is employed.

The N-terminal sequence can be altered by an ordinary DNA recombination technique, or specific site directional mutagenesis technique, a technique wherein PCR is used for the whole or partial length of MTG gene, or a technique wherein the part of the sequence to be altered is exchanged with a synthetic DNA fragment by a restriction enzyme treatment.

The transformant thus transformed with the recombinant DNA is cultured in a medium to produce a protein having a transglutaminase activity, and the protein is recovered. The methods for the preparation of the transformant and for the production of the protein are the same as those described above.

Since the protein thus produced has a sequence of Met-Ser-... from which the methionine residue is easily cleaved with methionine aminopeptidase, the methionine residue is cleaved in the cell of E. coli to obtain a protein that starts with serine residue.

Although MTG having N-terminal methionine residue is not present in the nature, the inventors have found that in some of natural MTG, aspartic acid residue is deleted to have N-terminal serine. Although a protein having N-terminal methionine residue is thus different from natural MTG in the sequence, a protein having N-terminal serine residue is included in the sequences of natural MTG and, in addition, a protein having such a sequence is actually present in the nature. Thus, it can be said that such MTG is equal to natural MTG. Namely, in the production of an enzyme to be used for foods, such as MTG, in which protein antigenicity is a serious problem, it is important to produce a protein having transglutaminase activity and also having a sequence equal to that of natural MTG, or in other words, to produce a sequence from which the N-terminal methionine residue was cleaved.

The following Examples will further illustrate the present invention, which by no means limit the invention.

EXAMPLE

Mass Production of MTG in E. coli

<1> Construction of MTG Expression Plasmid pTRPMTG-01:

MTG gene has been already completely synthesized, taking the frequency of using codons of E. coli and yeast into consideration (J. P. KOKAI No. Hei 5-199883). However, the gene sequence thereof was not optimum for the expression in E. coli. Namely, all of codons of thirty arginine residues were AGA (minor codons). Under these conditions, about 200 bases from the N-terminal of MTG gene were resynthesized to become a sequence optimum for the expression of E. coli.

As a promoter for transcripting MTG gene, trp promoter capable of easily deriving the transcription in a medium lacking tryptophane was used. Plasmid pTTG2-22 (J. P. KOKAI No. Hei 6-225775) for the high expression of transglutaminase (TG) gene of Pagrus major was obtained with trp promoter. The sequence in the upstream of the TG gene of Pagrus major was designed so that a foreign protein is highly expressed in E. coli.

In the construction of pTRPMTG-01, the DNA fragment from ClaI site in the downstream of trp promoter to BglII site in the downstream of Pagrus major's TG expression plasmid pTTG2-22 (J. P. KOKAI Hei 6-225775) was replaced with the ClaI/HpaI fragment of the synthetic DNA gene and the HpaI/BamHI fragment (small) of pGEM15BTG (J. P. KOKAI Hei 6-30771).

The ClaI/HpaI fragment of the Synthetic DNA gene has a base sequence from ClaI site in the downstream of trp promoter of pTTG2-22 to translation initiation codon, and 216 bases from the N-terminal of MTG gene. The base sequence in MTG structural gene was determined with reference to the frequency of using codon in E coli so as to be optimum for the expression in E. coli. However, for avoiding the high-order structure of mRNA, the third letter of the degenerated codon in the domain of encoding the N-terminal part was converted to a codon rich in adenine and uracil so as to avoid the arrangement of the same bases as far as possible.

The ClaI/HpaI fragment of the Synthetic DNA gene was so designed that it had EcoRI and HindIII sites at the terminal. The designed gene was divided into blocks each comprising about 40 to 50 bases so that the + chain and the − chain overlapped each other. Twelve DNA fragments corresponding to each sequence were synthesized (SEQ ID Nos. 4 to 15). 5' terminal of the synthetic DNA was phosphatized. Synthetic DNA fragments to be paired therewith were annealed, and they were connected with each other. After the acrylamide gel electrophoresis, the DNA fragments of an intended size was taken out and integrated in EcoRI/HindIII sites of pUC19. The sequence was confirmed and the correct one was named pUCN216. From the pUCN216, a ClaI/HpaI fragment (small) was taken out and used for the construction of pTRPMTG-01.

Figure 2:
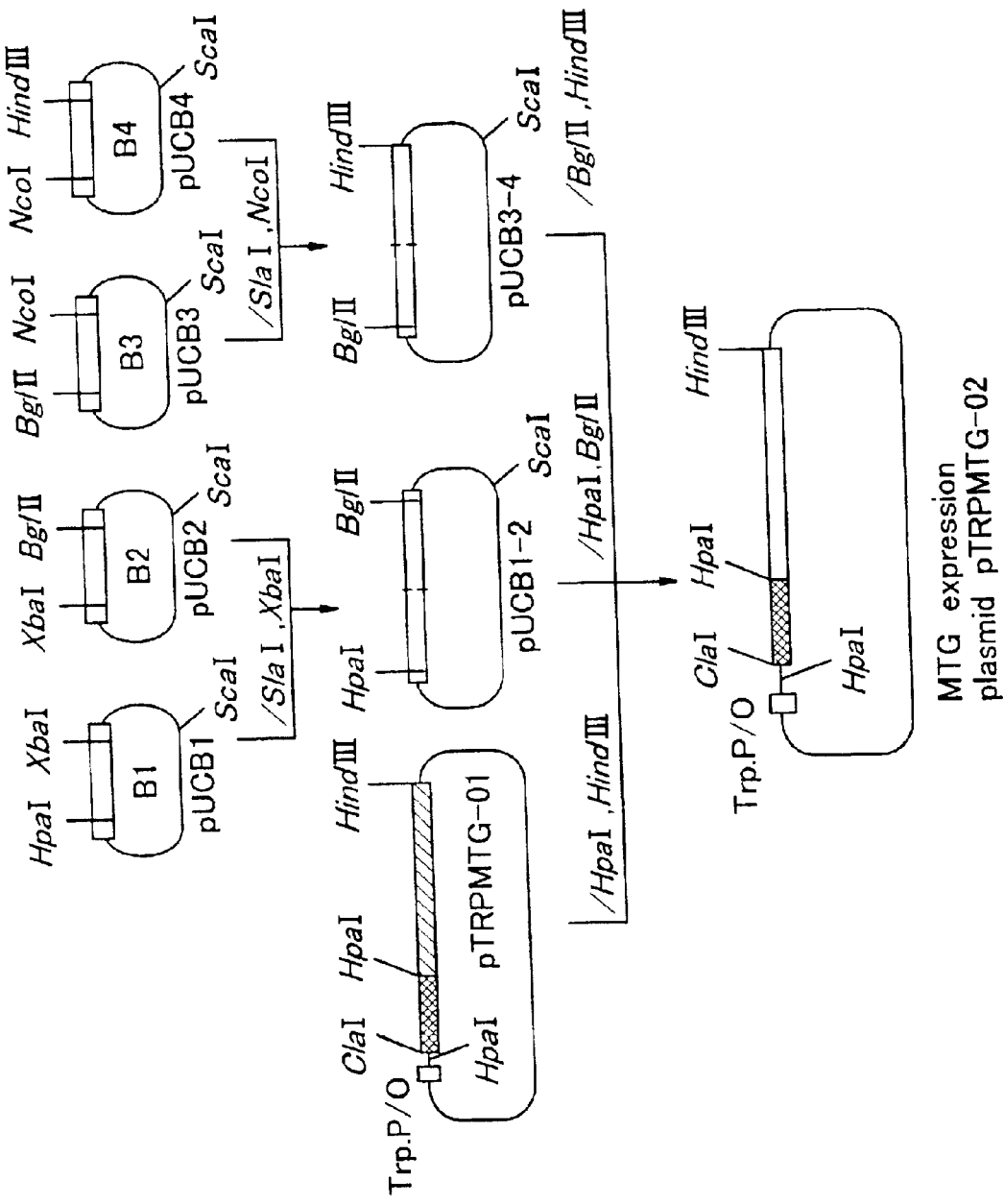
FIG. 2 shows a construction scheme of MTG expression plasmid pTRPMTG-02.

<2> Construction of MTG Expression Plasmid pTRPMTG-02:

Since E. coli JM109 keeping pTRPMTG-01 did not highly express MTG, parts (777 bases) other than the N-terminal altered parts of MTG gene were altered suitably for E. coli. Since it is difficult to synthesize 777 bases at the same time, the sequence was determined, taking the frequency of using codons in E. coli into consideration, and then four blocks (B1, 2, 3 and 4) therefor, each comprising about 200 bases, were synthesized. Each block was designed so that it had EcoRI/HindIII sites at the terminal. The designed gene was divided into blocks of about 40 to 50 bases so that the + chain and the − chain overlapped each other. Ten DNA fragments of the same sequence were synthesized for each block, and thus 40 blocks were synthesized in total (SEQ ID Nos. 16 to 55). 5' terminal of the synthetic DNA was phosphatized. Synthetic DNA fragments to be paired therewith were annealed, and they were connected with each other. After the acrylamide gel electrophoresis, DNA of an intended size was taken out and integrated in EcoRI/HindIII sites of pUC19. The base sequence of each of them was confirmed and the correct ones were named pUCB1, B2, B3 and B4. As shown in FIG. 2, B1 was connected with B2, and B3 was connected with B4. By replacing a corresponding part of pTRPMTG-01 therewith, pTRPMTG-02 was constructed. The sequence of the high expression MTG gene present on pTRPMTG-02 is shown in SEQ ID No. 3.

<3> Construction of MTG Expression Plasmid pUCTRPMTG-02(+), (−):

Since E. coli JM109 which keeps the pTRPMTG-02 also did not highly express MTG, the plasmid was multi-copied. EcoO109I fragment (small) containing trp promoter of pTRPMTG-02 was smoothened and then integrated into HincII site of pUC19 which is a multi-copy plasmid. pUCTRPMTG-02(+) in which lacZ promoter and trp promoter were in the same direction, and pUCTRPMTG-02(−) in which they were in the opposite direction to each other were constructed.

<4> Expression of MTG:

E. coli JM109 transformed with pUCTRPMTG-02(+) and pUC19 was cultured by shaking in 3 ml of 2xYT medium containing 150 μg/ml of ampicillin at 37° C. for ten hours (pre-culture). 0.5 ml of the culture suspension was added to 50 ml of 2xYT medium containing 150 μg/ml of ampicillin, and the shaking culture was conducted at 37° C. for 20 hours.

Figure 3:
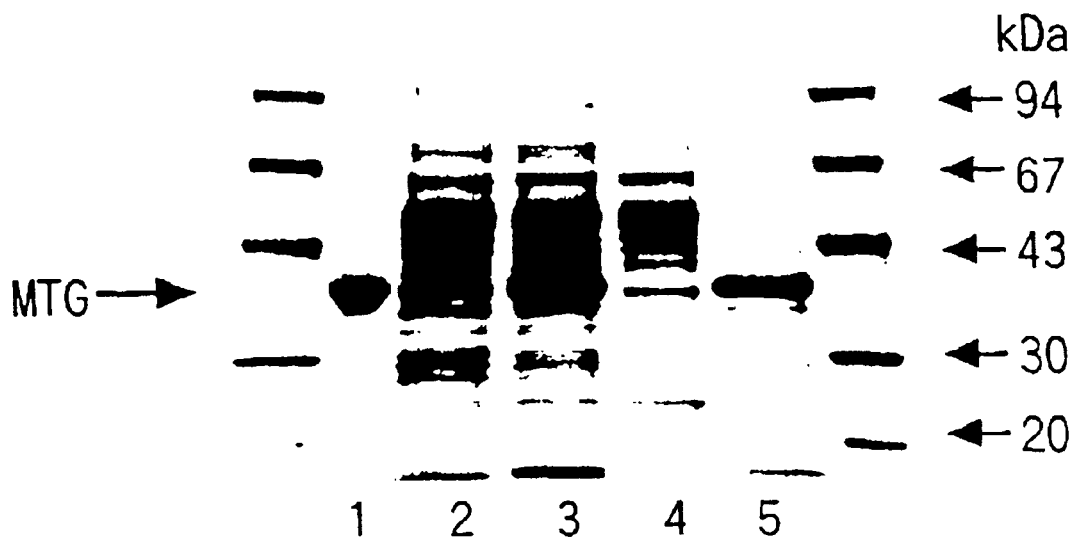
FIG. 3 is an expansion of SDS-polyacrylamide electrophoresis showing that MTG was expressed.
Figure 4:
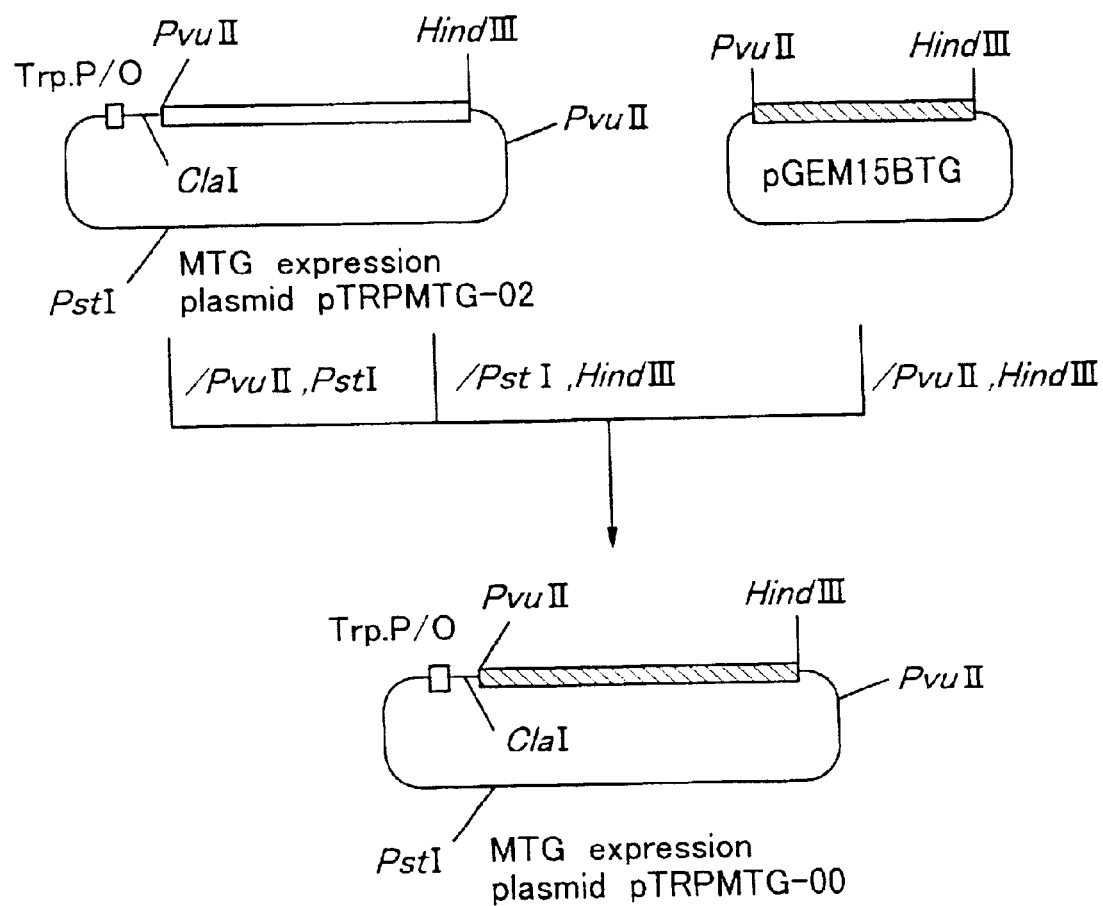
FIG. 4 shows a construction scheme of MTG expression plasmid pTRPMTG-00.

The cells were collected from the culture suspension and broken by ultrasonic disintegration. The results of SDS-polyacrylamide electrophoresis of the whole fraction, and supernatant and precipitation fractions both obtained by the centrifugation are shown in FIG. 3. The high expression of the protein having a molecular weight equal to that of MTG was recognized in the whole fraction of broken pUCTRPMTG-02(+)/JM109 cells and the precipitate fraction obtained by the centrifugation. It was confirmed by the western blotting that the protein was reactive with mice anti-MTG antibody. The expression of the protein was 500 to 600 mg/L. A sufficient, high expression was obtained even when 3-β-indole acrylic acid was not added to the production medium.

Further, the western blotting was conducted with MTG antibody against mouse to find that MTG was expressed only slightly in the supernatant fraction obtained by the centrifugation and that the expressed MTG was substantially all in the form of insoluble protein inclusion bodies.

<5> Construction of MTG Expression Plasmid pTRPMTG-00:

To prove that the change in codon of MTG gene caused a remarkable increase in the expression, pTRPMTG-00 corresponding to pTRPMTG-02 but in which MTG gene was changed to a gene sequence completely synthesized before (J. P. KOKAI No. Hei 6-30771) was constructed.

pTRPMTG-00 was constructed by connecting PvuII/PstI fragment (small) from Pagrus major's TG expression plasmid pTRPMTG-02 with PstI/HimdIII fragment (small, including PvuII site) and PvuII/HindIII fragment (small) of pGEM15BTG (J. P. KOKAI No. Hei 6-30771).

<6> Construction of MTG Expression Plasmid pUCTRPMTG-00(+), (−):

pTRPMTG-00 was multi-copied. EcoO109I fragment (small) containing trp promoter and trpA terminator of pTRPMTG-00 was smoothened and then integrated into HincII site of pUC19 which is a multi-copy plasmid. pUCTRPMTG-00(+) in which lacZ promoter and trp promoter were in the same direction, and pUCTRPMTG-00(−) in which they were in the opposite direction to each other were constructed.

<7> Comparison of MTG Expressions:

E. coli JM109 transformed with pUCTRPMTG-02 (+) or (−), pUCTRPMTG-00 (+) or (−), pTRPMTG-02, pTRPMTG-01, pTRPMTG-00 or pUC19 was cultured by shaking in 3 ml of 2xYT medium containing 150 μg/ml of ampicillin at 37° C. for ten hours (pre-culture). 0.5 ml of the culture suspension was added to 50 ml of 2xYT medium containing 150 μg/ml of ampicillin, and the shaking culture was conducted at 37° C. for 20 hours.

The cells were collected from the culture suspension, and MTG expression thereof was determined to obtain the results shown in Table 1. It was found that the newly constructed E. coli containing pTRPMTG-00, pUCTRPMTG-00 (+) or (−) did not highly express MTG. This result indicate that it is necessary for the high expression of MTG to change the codon of MTG gene into a codon for E. coli and also to multi-copy the plasmid.

TABLE 1

| Strain | MTG expression |
|---|---|
| pUCTRPMTG-02(+)/JM109 | +++ |
| pUCTRPMTG-02(−)/JM109 | +++ |
| pUCTRPMTG-00(+)/JM109 | + |
| pUCTRPMTG-00(−)/JM109 | + |
| pTRPMTG-02/JM109 | + |
| pTRPMTG-01/JM109 | + |
| pTRPMTG-00/JM109 | − |
| pUC19/JM109 | − |

+++: at least 300 mg/l
+: 5 mg/l or below
−: no expression

<8> Analysis of N-terminal Amino Acid of Expressed MTG:

The N-terminal amino acid residue of the protein inclusion bodies of expressed MTG was analyzed to find that about 60% of the sequence of N-terminal was methionine residue and about 40% thereof was formylmethionine residue. (Formyl)methionine residue corresponding to the initiation codon was removed by a technical idea described below.

<9> Deletion of N-terminal Aspartic Acid Residue of MTG:

A base sequence corresponding to aspartic acid residue (the N-terminal of MTG) was deleted by PCR using pUCN216 containing 216 bases as the template. pUCN216 is a plasmid obtained by cloning about 216 bp's containing ClaI-HpaI fragment of N-terminal of MTG in EcoRI/HindIII site of pUC19. pF01 (SEQ ID No. 56) and pR01 (SEQ ID No. 57) are primers each having a sequence in the vector. pDELD (SEQ ID No. 58) is that obtained by deleting a base sequence corresponding to Asp residue. pHd01 (SEQ ID No. 59) is that obtained by replacing C with G not to include HindIII site. pF01 and pDELD are sense primers and pR01 and pHd01 are antisense primers.

35 cycles of PCR of a combination of pF01 and pHd01, and a combination of pELD and pR01 for pUCN216 was conducted at 94° C. for 30 seconds, at 55° C. for one minute and at 72° C. for two minutes. Each PCR product was extracted with phenol/chloroform, precipitated with ethanol and dissolved in 100 μl of H₂O.

1 μl of each of the PCR products was taken, and they were mixed together. After the heat denaturation at 94° C. for 10 minutes, 35 cycles of PCR of a combination of pF01 and pHd01 was conducted at 94° C. for 30 seconds, at 55° C. for one minute and at 72° C. for two minutes.

Figure 5:
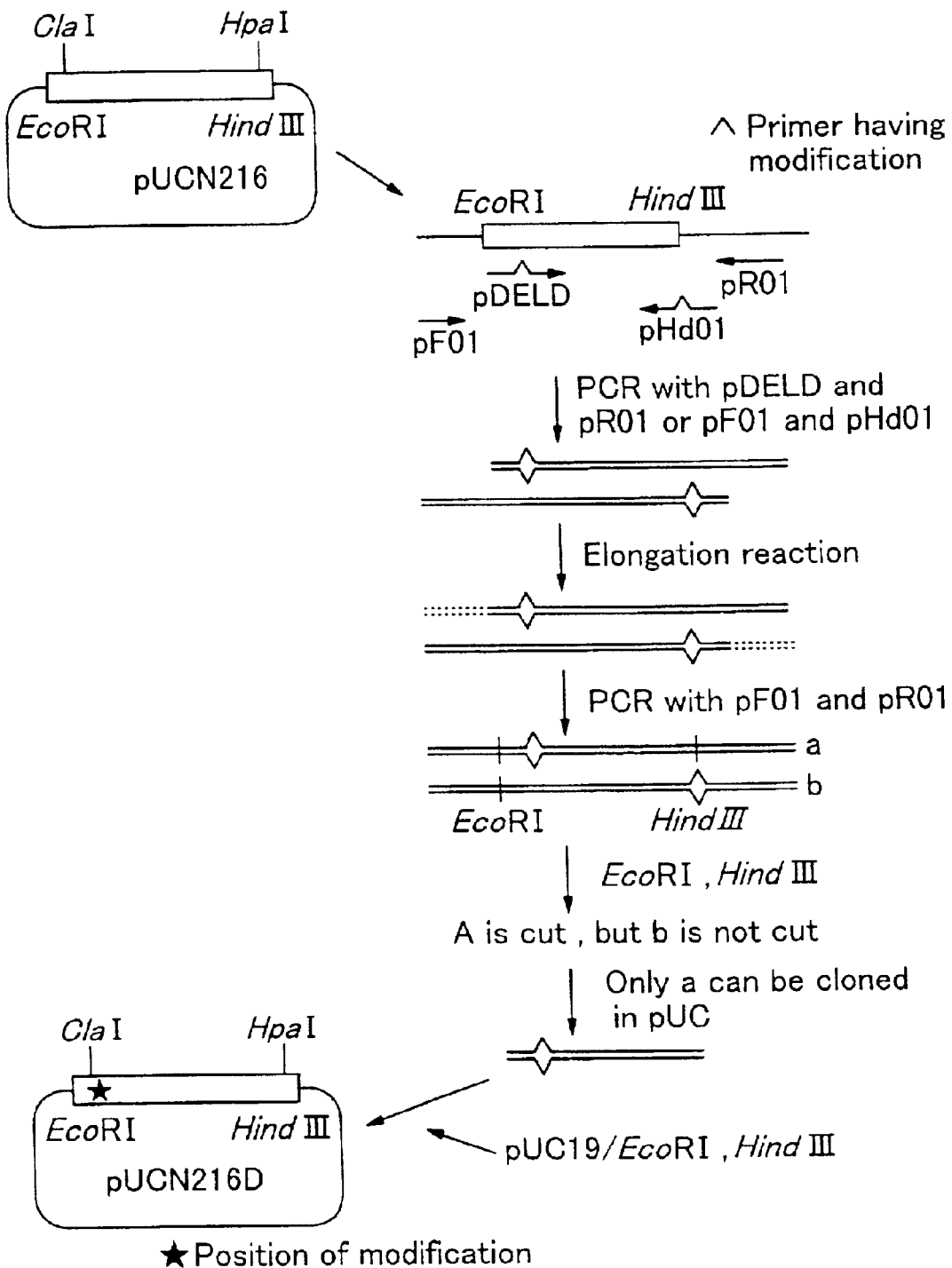
FIG. 5 shows a construction scheme of plasmid pUCN216D.

The second PCR product was extracted with phenol/chloroform, precipitated with ethanol, and treated with HindIII and EcoRI. After pUC19 subcloning, pUCN216D was obtained (FIG. 5). The sequence of the obtained pUCN216D was confirmed to be the intended one.

Figure 6:
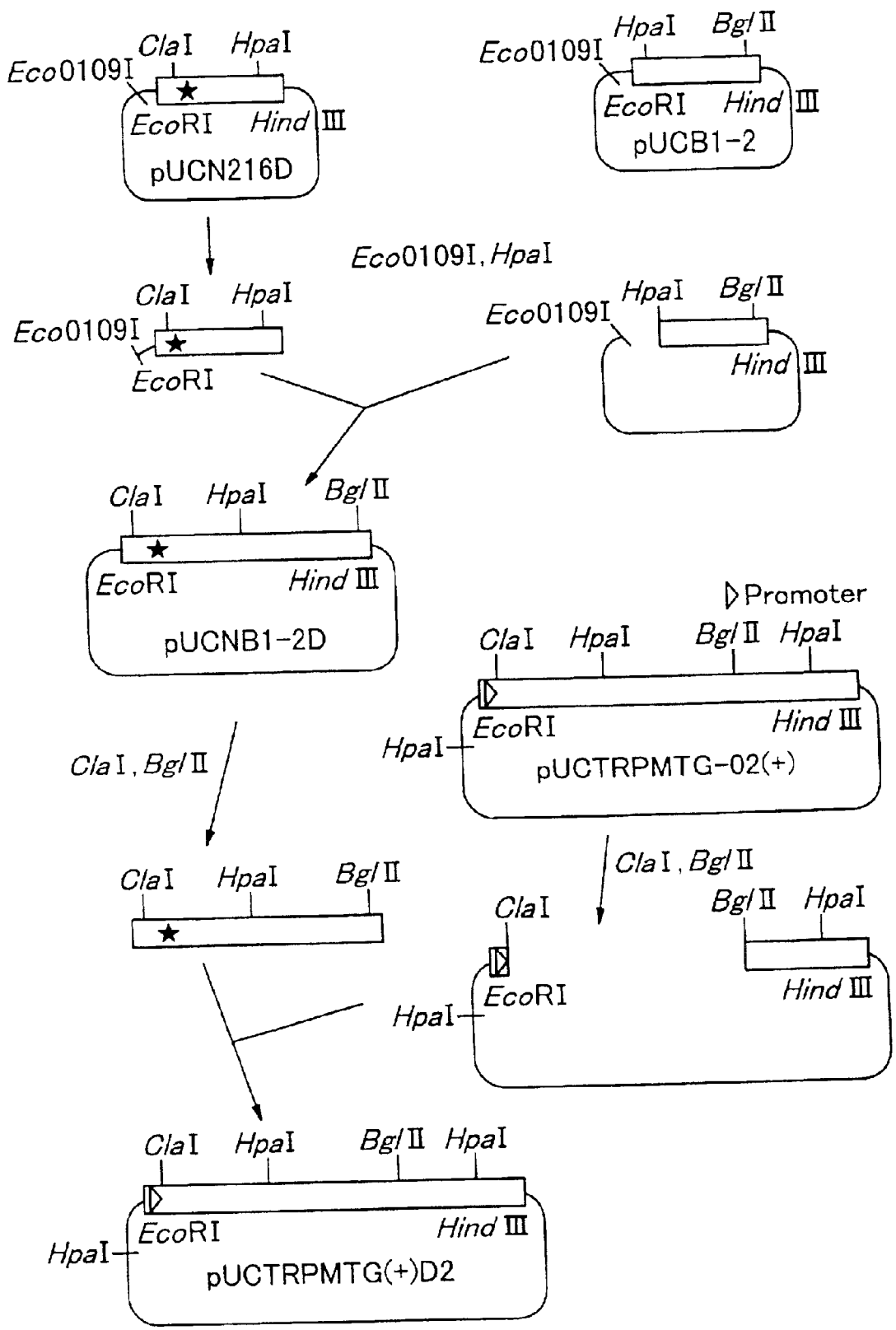
FIG. 6 shows a construction scheme of MTG expression plasmid pUCTRPMTG(+)D2.

<10> Construction of the Plasmid Encoding for MTG which Lacks N-terminal Aspartic Acid:

EcoO109I/HpaI fragment (small) of pUCN216D was combined with EcoO109I/HpaI fragment (large) of pUCBl-1 (plasmid obtained by cloning HpaII/Bg1II fragment of MTG gene in EcoRI/HindIII site of pUC19) to obtain pUCNB1-2D. Further, ClaI/Bg1 II fragment (small) of pUCNB1-2D was combined with ClaI/B/Bg1III fragment (large) of pUCTRPMTG-02(+) which is a plasmid of high MTG expression to obtain pUC TRPMTG(+)D2, the expression plasmid of MTG which lacks N-termianl aspertic acid(FIG. 6). As a result, a plasmid containing MTG gene lacking GAI corresponding to aspartic acid residue as shown in FIG. 7 was obtained.

<11> Expression of the Plasmid Encoding for MTG which Lacks N-terminal Aspartic Acid:

E. coli JM109 transformed with pUCTRPMTG(+)D2 was cultured by shaking in 3 ml of 2xYT medium containing 150 μg/ml of ampicillin at 37° C. for ten hours (pre-culture). 0.5 ml of the culture suspension was added to 50 ml of 2xYT medium containing 150 μg/ml of ampicillin, and the shaking culture was conducted at 37° C. for 20 hours. The cells were broken by the ultrasonic disintegration. The results of the dyeing with Coomassie Brilliant Blue dyeing and Western blotting with mouse antiMTG antibody of the thus obtained supernatant liquid and precipitate indicated that MTG protein lacking N-terminal aspartic acid residue was detected in the precipitate obtained by the ultrasonic disintegration, namely in the insoluble fraction. This fact suggests that MTG protein lacking N-terminal aspartic acid residue was accumulated as protein inclusion bodies in the cells.

The N-terminal amino acid sequence of the protein inclusion bodies was analyzed to find that about 90% thereof was serine as shown in FIG. 8.

The results of the analysis of N-terminal amino acids of expressed MTG obtained in <8> and <11> were compared with each other as shown in Table 2. It was found that by deleting the N-terminal aspartic acid residue from MTG, the initiation methionine added to the N-terminal of the expressed MTG was efficiently removed.

TABLE 2

| | N-terminal amino acid | | | |
|---|---|---|---|---|
| Strain | f-Met | Met | Asp | Ser |
| pUCTRPMTG-02(+)/JM109 | 40% | 60% | N.D. | |
| pUCTRPMTG(+)D2/JM109 | N.D. | 10% | — | 90% |

<12> Solubilization of MTG Inclusion Bodies Lacking N-terminal Aspartic Acid Residue, Renaturation of Activity and Determination of Specific Activity:

MTG inclusion bodies lacking aspartic acid was partially purified by repeating the centrifugation several times, and then dissolved in 8 M urea [50 mM phosphate buffer (pH 5.5)] to obtain the 2 mg/ml solution. Precipitates were removed from the solution by the centrifugation and the solution was diluted to a concentration of 0.5 M urea with 50 mM phosphate buffer (pH 5.5). The diluted solution was further dialyzed with 50 mM phosphate buffer (pH 5.5) to remove urea. According to Mono S column test, the peak having TG activity was eluted when NaCl concentration was in the range of 100 to 150 mM. The specific activity of the fraction was determined by the hydroxamate method to find that the specific activity of the aspartic acid residue-lacking MTG was about 30 U/mg. This is equal to the specific activity of natural MTG. It is thus apparent that the lack of aspartic acid residue exerts no influence on the specific activity.

What is claimed is:

1. An isolated protein having a transglutaminase activity, wherein the amino acid sequence of the protein comprises the serine residue at the second position to the proline residue at the 331st position of the amino acid sequence of SEQ ID No: 1, wherein the N-terminal amino acid of the protein is the serine residue at the second position of SEQ ID No: 1.

2. The protein of claim 1, wherein the amino acid sequence of the protein consists of the serine residue at the second position to proline residue at the 331st position of the amino acid sequence of SEQ ID No: 1.1.

3. The protein of claim 1, wherein said protein is isolated from a bacterial culture.

4. A method of catalyzing acyl transfer of a γ-carboxyamido group in a peptide chain of a protein having at least one glutamine residue comprising contacting said protein having at least one glutamine residue with the protein of claim 1.

5. A method of producing gelled food comprising mixing the protein of claim 1 with the ingredients of said gelled food.

6. The method of claim 5, wherein said gelled food is a jelly, a yogurt, or a cheese.

7. A method of producing gelled cosmetic comprising mixing the protein of claim 1 with the ingredients of said gelled cosmetic.

8. The protein of claim 2, wherein said protein is isolated from a bacterial culture.

9. A method of catalyzing acyl transfer of a γ-carboxyamido group in a peptide chain of a protein having at least one ghitamine residue comprising contacting said protein having at least one glutamine residue with the protein of claim 2.

10. A method of producing gelled food comprising mixing the protein of claim 2 with the ingredients of said gelled food.

11. The method of claim 10, wherein said gelled food is a jelly, a yogurt, or a cheese.

12. A method of producing gelled cosmetic comprising mixing the protein of claim 2 with the ingredients of said gelled cosmetic.

* * * * *